US009395346B2

(12) United States Patent
Walukas et al.

(10) Patent No.: US 9,395,346 B2
(45) Date of Patent: Jul. 19, 2016

(54) NON-CONTACT EGG IDENTIFICATION SYSTEM FOR DETERMINING EGG VIABILITY, AND ASSOCIATED METHOD

(71) Applicant: Zoetis Services LLC, Florham Park, NJ (US)

(72) Inventors: Joel James Walukas, Cary, NC (US); Ramin Karimpour, Raleigh, NC (US)

(73) Assignee: Zoetis Services LLC, Florham Park, NJ (US)

( * ) Notice: Subject to any disclaimer, the term of this patent is extended or adjusted under 35 U.S.C. 154(b) by 0 days.

(21) Appl. No.: 14/536,855

(22) Filed: Nov. 10, 2014

(65) Prior Publication Data

US 2015/0136988 A1  May 21, 2015

Related U.S. Application Data

(60) Provisional application No. 61/905,385, filed on Nov. 18, 2013.

(51) Int. Cl.
*G01J 5/02* (2006.01)
*G01N 33/08* (2006.01)
(Continued)

(52) U.S. Cl.
CPC ............... *G01N 33/08* (2013.01); *A01K 43/00* (2013.01); *A01K 45/007* (2013.01); *A61B 5/024* (2013.01);
(Continued)

(58) Field of Classification Search
CPC .......... G01N 33/085; G01N 2201/062; G01N 21/3563; G01N 21/59; G01N 2201/061; G01N 2201/125; G01N 33/08; A61B 17/435; A61B 2503/40; A61B 5/024; A61B 5/704; A01K 43/00; A01K 45/007
USPC ...................................................... 250/341.1
See application file for complete search history.

(56) References Cited

U.S. PATENT DOCUMENTS 2,186,196 A * 1/1940 Haugh ................. G01N 33/085
209/511
2,987,182 A * 6/1961 Ator ....................... A01K 43/00
209/511
(Continued)

FOREIGN PATENT DOCUMENTS

FR 2455282 A1 11/1980
JP 09127096 A 5/1997
(Continued)

OTHER PUBLICATIONS

Lin Yang et al., 2012, Noninvasive vasculature detection using laser speckle imaging in avian embryos through intact egg in early incubation stage, Biomedical Optics Express, vol. 4, pp. 32-37.
(Continued)

*Primary Examiner* — David J Makiya
*Assistant Examiner* — Taeho Jo
(74) *Attorney, Agent, or Firm* — Scott C. Mayhew (57) ABSTRACT

An egg identification system for determining viability of an avian egg is provided. Such a system includes an emitter assembly configured to emit electromagnetic radiation toward an egg. A detector assembly is axially aligned with the emitter assembly to detect electromagnetic radiation transmitted through the egg. The detector assembly is spaced-apart from the egg during operation thereof such that the detector assembly does not contact the egg. The detected electromagnetic radiation is used to generate an output signal. The output signal is processed to determine whether there exists a periodic variation or an aperiodic perturbation in an intensity of the electromagnetic radiation transmitted through the egg corresponding to action of a heart or embryo movement, wherein the existence of the periodic variation or aperiodic perturbation indicates that the egg is viable. An associated method is also provided.

14 Claims, 10 Drawing Sheets

(51) Int. Cl.
  *A01K 43/00* (2006.01)
  *A61B 5/024* (2006.01)
  *G01N 21/3563* (2014.01)
  *G01N 21/59* (2006.01)
  *A01K 45/00* (2006.01)
  *A61B 5/00* (2006.01)

(52) U.S. Cl.
  CPC ............ *A61B 5/704* (2013.01); *G01N 21/3563* (2013.01); *G01N 21/59* (2013.01); *G01N 33/085* (2013.01); *A61B 2503/40* (2013.01); *G01N 2201/062* (2013.01); *G01N 2201/125* (2013.01)

(56) References Cited

U.S. PATENT DOCUMENTS

| | | | |
|---|---|---|---|
| 3,060,794 A * | 10/1962 | Reading | A01K 43/00 209/511 |
| 3,540,824 A | 11/1970 | Fonda et al. | |
| 3,740,144 A * | 6/1973 | Walker | G01J 3/433 356/229 |
| 4,017,192 A | 4/1977 | Rosenthal | |
| 4,037,151 A | 7/1977 | Takeuchi | |
| 4,039,259 A | 8/1977 | Saito et al. | |
| 4,671,652 A | 6/1987 | van Asselt et al. | |
| 4,955,728 A | 9/1990 | Hebrank | |
| 5,173,737 A | 12/1992 | Mitchell et al. | |
| 5,504,572 A | 4/1996 | Taylor et al. | |
| 5,745,228 A | 4/1998 | Hebrank et al. | |
| 5,853,372 A | 12/1998 | Britton | |
| 6,234,320 B1 * | 5/2001 | Hebrank | A01K 43/00 209/51 |
| 6,488,156 B1 | 12/2002 | Cohen | |
| 6,535,277 B2 | 3/2003 | Chalker, II et al. | |
| 6,860,225 B2 | 3/2005 | Hebrank | |
| 7,034,302 B2 * | 4/2006 | Davidson | G01N 21/3577 250/339.06 |
| 7,154,594 B2 | 12/2006 | Reeves et al. | |
| 7,289,196 B2 | 10/2007 | Reeves et al. | |
| 8,107,060 B2 | 1/2012 | Hebrank et al. | |
| 8,933,405 B2 * | 1/2015 | Diamond | G01N 21/4795 250/339.07 |
| 2002/0075476 A1 * | 6/2002 | Chalker, II | A01K 43/00 356/53 |
| 2003/0227613 A1 * | 12/2003 | Hebrank | C12N 7/00 356/52 |
| 2004/0065263 A1 * | 4/2004 | Hebrank | A01K 43/00 119/6.8 |
| 2004/0107912 A1 * | 6/2004 | Hebrank | A01K 45/007 119/6.8 |
| 2006/0156989 A1 * | 7/2006 | Hebrank | A01K 45/007 119/6.8 |
| 2006/0278831 A1 * | 12/2006 | Matsumoto | G01N 21/59 250/341.1 |
| 2007/0024844 A1 * | 2/2007 | Hebrank | G01N 33/085 356/53 |
| 2008/0252877 A1 * | 10/2008 | Kok | G01N 21/314 356/53 |
| 2010/0025586 A1 * | 2/2010 | Ogawa | G01N 21/3581 250/341.1 |
| 2011/0092762 A1 * | 4/2011 | Wong | C12N 5/0604 600/34 |
| 2012/0267534 A1 * | 10/2012 | Ijuin | G01M 3/38 250/341.8 |
| 2013/0015354 A1 * | 1/2013 | Diamond | G01N 21/4795 250/339.07 |
| 2013/0017296 A1 * | 1/2013 | Chait | A23L 1/32 426/87 |
| 2014/0367316 A1 * | 12/2014 | Saeedkia | B07C 5/344 209/577 |

FOREIGN PATENT DOCUMENTS

| | | |
|---|---|---|
| JP | 2001041882 A2 | 2/2001 |
| JP | 2013242190 A2 | 12/2013 |
| JP | 2014153333 A2 | 8/2014 |
| SU | 1597173 A1 | 10/1990 |
| WO | WO 98/14781 A1 | 4/1998 |

OTHER PUBLICATIONS

International Search Report and Written Opinion, International Application No. PCT/US2014/065870, date of mailing Feb. 4, 2015.
Hirota et al., "Optical Studies of Excitation-Contraction Coupling in the Early Embryonic Chick Heart," J. Physiol., 1985, vol. 366, pp. 89-106.
Lewin et al., "Pulse oximetry: a new way of determining the heart rate in chicken embryos," 1997, Eur. J. Physiol., vol. 434, pp. 639-641.

\* cited by examiner

NON-CONTACT EGG IDENTIFICATION SYSTEM FOR DETERMINING EGG VIABILITY, AND ASSOCIATED METHOD

CROSS REFERENCE TO RELATED APPLICATION

This application claims the benefit of U.S. Provisional Patent Application No. 61/905,385, filed Nov. 18, 2013, which is expressly incorporated herein by reference in its entirety.

TECHNICAL FIELD

The present disclosure generally relates to egg identification systems. More particularly, the present disclosure relates to a non-contact egg identification system capable of determining whether a viable embryo is present within an avian egg by using an emitter-detector system, and an associated method.

BACKGROUND

Discrimination between poultry eggs on the basis of some observable quality is a well-known and long-used practice in the poultry industry. "Candling" is a common name for one such technique, a term which has its roots in the original practice of inspecting an egg using the light from a candle. As is known to those familiar with eggs, although egg shells appear opaque under most lighting conditions, they are in reality somewhat translucent, and when placed in front of direct light, the contents of the egg can be observed.

Eggs which are to be hatched to live poultry are typically candled during embryonic development to identify clear, rotted, and dead eggs (collectively referred to herein as "non-live eggs"). Non-live eggs (also referred to as non-viable eggs) are removed from incubation to increase available incubator space and also reduce the risk of bio-contamination. In many instances it is desirable to introduce a substance, via in ovo injection, into a live egg (also referred to as a viable egg) prior to hatch. Injections of various substances into avian eggs are employed in the commercial poultry industry to decrease post-hatch mortality rates or increase the growth rates of the hatched bird. Examples of substances that have been used for, or proposed for, in ovo injection include vaccines, antibiotics and vitamins.

In ovo injections of substances typically occur by piercing an egg shell to create a hole therethrough (e.g., using a punch or drill), extending an injection needle through the hole and into the interior of the egg (and in some cases into the avian embryo contained therein), and injecting one or more treatment substances through the needle. Such devices may position an egg and an injection needle in a fixed relationship to each other, and may be designed for the high-speed automated injection of a plurality of eggs. The selection of both the site and time of injection treatment can also impact the effectiveness of the injected substance, as well as the mortality rate of the injected eggs or treated embryos.

In commercial poultry production, only about 60% to 90% of commercial broiler eggs hatch. Eggs that do not hatch include eggs that were not fertilized, as well as fertilized eggs that have died. Infertile eggs may comprise from about 5% up to about 25% of all eggs in a set. Due to the number of non-live eggs encountered in commercial poultry production, the use of automated methods for in ovo injection, and the cost of treatment substances, an automated method for identifying live eggs and selectively injecting (or selectively contacting) only live eggs, is desirable.

Figure 1:
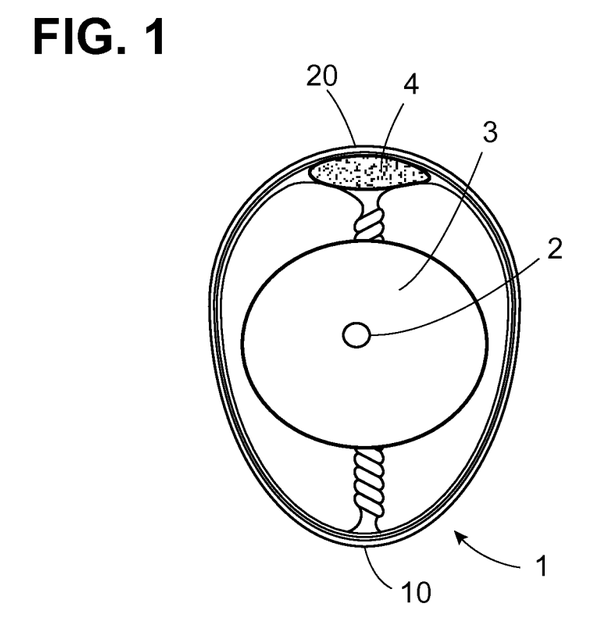
FIG. 1 illustrates a live chicken egg at about day one of incubation.
Figure 2:
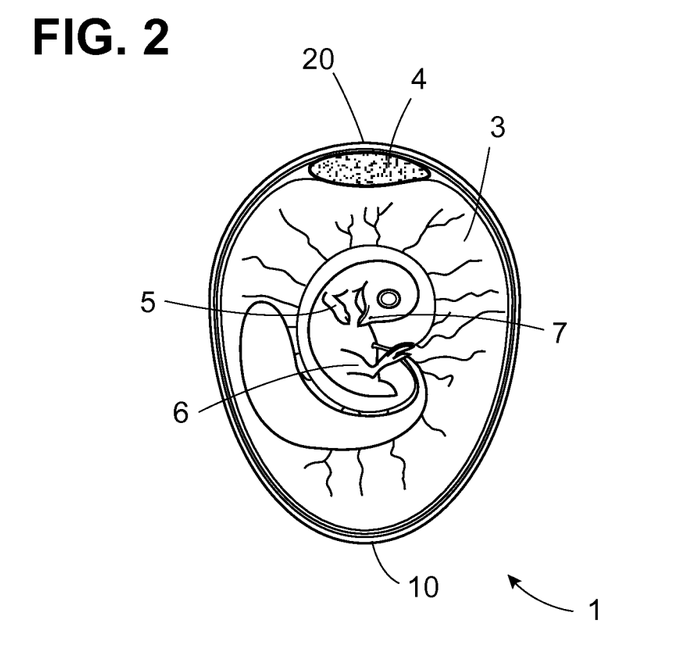
FIG. 2 illustrates a live chicken egg at about day eleven of incubation.

An egg may be a "live" egg, meaning that it has a viable embryo. FIG. 1 illustrates a live poultry egg 1 at about day one of incubation. FIG. 2 illustrates the live egg 1 at about day eleven of incubation. The egg 1 has a somewhat narrow end in the vicinity represented at 10 as well as an oppositely disposed broadened or blunt end portion in the vicinity shown at 20. In FIG. 1, an embryo 2 is represented atop the yolk 3. The egg 1 contains an air cell 4 adjacent the broadened end 20. As illustrated in FIG. 2, the wings 5, legs 6, and beak 7 of a baby chick have developed.

An egg may be a "clear" or "infertile" egg, meaning that it does not have an embryo. More particularly, a "clear" egg is an infertile egg that has not rotted. An egg may be an "early dead" egg, meaning that it has an embryo which died at about one to five days old. An egg may be a "mid-dead" egg, meaning that it has an embryo which died at about five to fifteen days old. An egg may be a "late-dead" egg, meaning that it has an embryo which died at about fifteen to eighteen days old.

An egg may be a "rotted" egg, meaning that the egg includes a rotted infertile yolk (for example, as a result of a crack in the egg's shell) or, alternatively, a rotted, dead embryo. While an "early dead," "mid-dead" or "late-dead egg" may be a rotted egg, those terms as used herein refer to such eggs which have not rotted. Clear, early-dead, mid-dead, late-dead, and rotted eggs may also be categorized as "non-live" eggs because they do not include a living embryo.

There are other applications where it is important to be able to distinguish between live (viable) and non-live (non-viable) eggs. One of these applications is the cultivation and harvesting of vaccines via live eggs (referred to as "vaccine production eggs"). For example, human flu vaccine production is accomplished by injecting seed virus into a chicken egg at about day eleven of embryonic development (Day-11 egg), allowing the virus to grow for about two days, euthanizing the embryo by cooling the egg, and then harvesting the agnostic fluid from the egg. Typically, eggs are candled before injection of a seed virus to remove non-live eggs. Vaccine production eggs may be candled one or more days prior to injection of a seed virus therein. Identification of live eggs in vaccine production is important because it is desirable to prevent seed vaccine from being wasted in non-live eggs and to reduce costs associated with transporting and disposing of non-live eggs.

Some previous candling apparatuses have employed opacity identification systems in which a plurality of light sources and corresponding light detectors are mounted in an array, and wherein eggs are passed on a flat between the light sources and the light detectors. Unfortunately, such conventional candling techniques may have somewhat limited accuracy due to different categories of eggs having similar optical densities (e.g., live and rotted) resulting in similar levels of transmitted light. Light opacity identification systems can operate at speeds equivalent to about 300,000 eggs per hour and successfully identify clear eggs from a stream of eggs. However, some eggs identified as being live may in fact be non-live (e.g., rotted eggs, mid and late dead eggs).

Other previous candling apparatuses have employed embryo heartbeat detection capable of detecting live and non-live eggs. However, these systems require the detection tooling to contact the eggs in order to create a mechanical light seal for detection purposes, which may present several problems. First, the throughput parameter is slowed down because the eggs must be stopped while the detection tooling head is lowered and raised in order for each detection tooling to contact a respective egg. Next, mechanical contact with the non-live eggs, particularly with the rotted eggs (which can explode when contacted), may undesirably introduce contamination into the detection system, which could potentially be transferred to subsequent live eggs during further processing. Finally, the emitter-detector configurations in previous heartbeat detection systems are difficult to position mechanically to allow for desired throughput, wherein incomplete sealing may result in light leakage interfering with the desired transmitted signal.

Accordingly, it would be desirable to provide a candling apparatus implementing a heartbeat detection system capable of accurately distinguishing live and non-live eggs without making contact therewith during operation and without the use of a mechanical light seal. Furthermore, it would be desirable to provide an associated method that would facilitate heartbeat detection of live eggs in a high throughput and accurate manner.

BRIEF SUMMARY

The above and other needs are met by aspects of the present disclosure which, according to one aspect, provides an egg identification system for determining viability of an avian egg. The system includes a conveyor system configured to convey an egg flat containing a plurality of egg. An emitter assembly is configured to emit collimated electromagnetic radiation toward one of the eggs conveyed in the egg flat. A non-contact detector assembly is axially aligned with the emitter assembly. The non-contact detector assembly is configured to detect the electromagnetic radiation transmitted through the egg. The non-contact detector assembly is disposed in a non-contact position such that an egg positioned for identification is spaced-apart from the non-contact detector assembly during operation thereof. A processor is configured to process an output signal of the non-contact detector assembly to determine whether there exists a periodic or aperiodic variation in an intensity of the electromagnetic radiation transmitted through a respective egg corresponding to action of a heart or embryo movement, the existence of the periodic or aperiodic variation indicating that the egg is viable.

Another aspect provides a method of determining viability of an egg. The method comprises conveying an egg contained in an egg flat using a conveyor system. The method further comprises emitting collimated electromagnetic radiation from an emitter assembly toward the egg. The method further comprises detecting electromagnetic radiation transmitted through the egg with a non-contact detector assembly axially aligned with the emitter assembly, the non-contact detector assembly being spaced-apart from the egg. The method further comprises generating an output signal from the electromagnetic radiation detected by the non-contact detector assembly. The method further comprises processing the output signal to determine whether there exists a periodic or aperiodic variation in an intensity of the electromagnetic radiation transmitted through a respective egg corresponding to action of a heart or embryo movement, the existence of the periodic or aperiodic variation being indicative that the egg is viable.

Thus, various aspects of the present disclosure provide advantages, as otherwise detailed herein.

BRIEF DESCRIPTION OF THE DRAWINGS

Having thus described various embodiments of the present disclosure in general terms, reference will now be made to the accompanying drawings, which are not necessarily drawn to scale, and wherein:

DETAILED DESCRIPTION OF THE DISCLOSURE

Various aspects of the present disclosure now will be described more fully hereinafter with reference to the accompanying drawings, in which some, but not all aspects of the disclosure are shown. Indeed, this disclosure may be embodied in many different forms and should not be construed as limited to the aspects set forth herein; rather, these aspects are provided so that this disclosure will satisfy applicable legal requirements. Like numbers refer to like elements throughout.

The present disclosure is directed to systems and methods for accurately determining the viability of a plurality of eggs in a high throughput manner without contacting the eggs as the eggs pass through an identification means. Passing of the eggs through the system in a non-contact or contactless manner provides many advantages, including maintaining stationary position of the detection system components to improve throughput and limiting contact with non-live eggs such as rotted eggs that may explode.

As used herein, the terms "non-contact" and "contactless" refer to maintaining a spaced-apart relationship between the egg and certain components of the egg identification system disclosed herein during operation of the emitter-detector pairs when determining viability. In some instances, this may specifically refer to the spaced-apart relationship of the detector assembly to the egg. In this regard, the detector assembly of the present disclosure may be positioned apart from the egg such that no component thereof contacts the egg, thereby eliminating any mechanical light seal capable of limiting interfering signals from being detected. Instead, the present disclosure deals with rejecting these interfering signals by other means in such a manner that contact with the egg is not required. Of course, the eggs may be in contact with a carrier means, such as an egg flat, configured to transport the eggs through the egg identification system. In this regard, the term "non-contact" refers to the avoidance of contact between the eggs and the operating components of the egg identification system.

Furthermore, the present disclosure is directed to systems and methods using transmission (so-called "through beam") modes for determining viability of an egg. By operating in a transmission mode, the emitter and detector of the egg identification system may be axially aligned along a common longitudinal axis such that the system may be configured in a workable manner. That is, the system configuration doesn't have to account for an emitter-detector pair operating in a reflectance mode and having an emitter and detector arranged, for example, at right angles for receiving a reflectance signal. Instead, the emitter assembly and the detector assembly may be positioned on opposite sides of the eggs such that the eggs can easily pass therebetween for evaluation and identification.

However, because aspects of the present disclosure may operate in a non-contact and transmission manner, the desired transmitted light levels may be low while the potential for undesirable interference signals may be high. In this regard, further aspects of the present disclosure are provided such that the undesired interference signal may be limited and the desired low transmission signal (less than about 1 nW/cm$^2$) may be maximized for processing so as to provide accurate and reliable identification of viable eggs.

The methods and systems according to aspects of the present disclosure may be utilized for accurately identifying live and non-live eggs at any time during embryonic development (also referred to as the incubation period). Aspects of the present disclosure are not limited to identification only at a particular day (e.g., day eleven) or time period during the embryonic development period. In addition, methods and apparatus according to aspects of the present disclosure may be used with any types of avian eggs including, but not limited to, chicken, turkey, duck, geese, quail, pheasant eggs, exotic bird eggs, etc.

Figure 3:
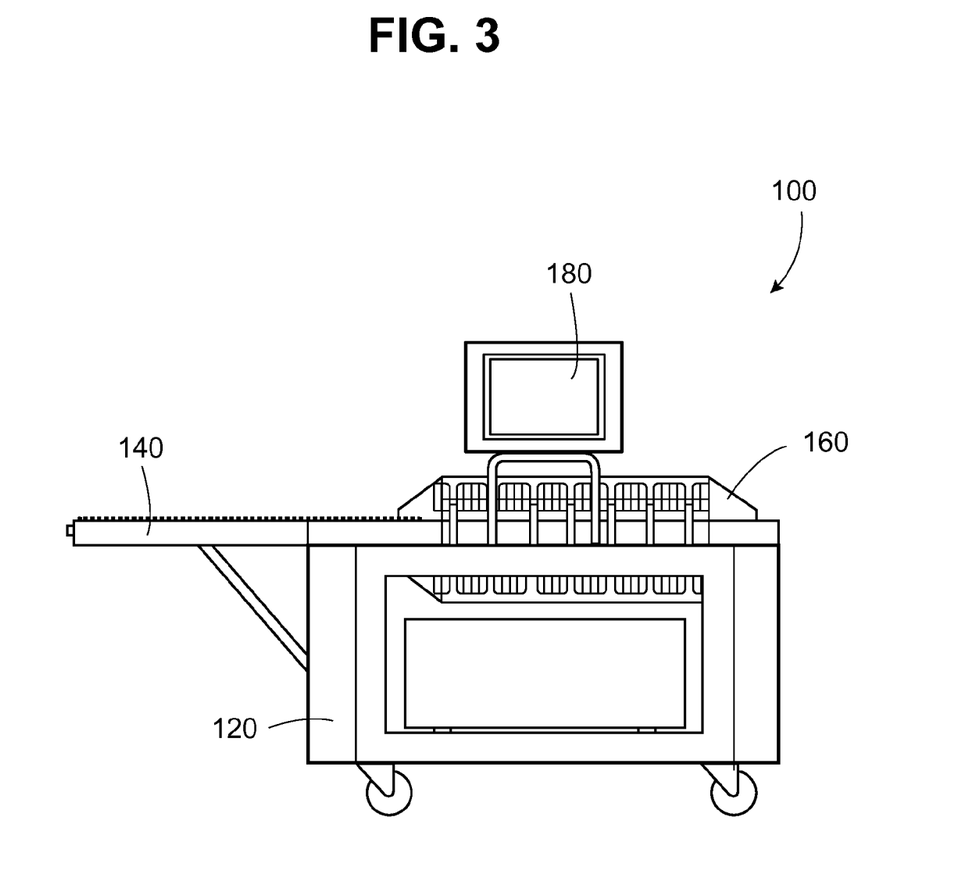
FIG. 3 is a schematic view of an egg identification system, according to one aspect of the present disclosure.

FIG. 3 illustrates an egg identification system 100 capable of implementing various aspects of the present disclosure. The egg identification system 100 may include a frame 120 and a conveyor system 140 configured to convey a plurality of eggs contained in an egg flat 50 (FIG. 4) to an egg detection system 160. In some instances, the egg identification system may include a display 180 capable of displaying information related to the egg identification system and/or the eggs passing through the egg detection system 160 for identification thereof. The egg identification system 100 may include a controller for controlling various aspects of thereof, including the ability to enable and disable certain components of the egg detection system 160. The egg identification system 100 may be portable and, in some instances, may be configured in a modular manner such that it may be connected to other associated devices, such as, for example, an egg injection apparatus, an egg sorting apparatus, an egg transfer apparatus, an egg remover apparatus, or a gender identification apparatus. In some instances, the egg detection system 160 may be directly applied to an egg injection apparatus, an egg sorting apparatus, an egg transfer apparatus, an egg remover apparatus, or a gender identification apparatus.

Figure 4:
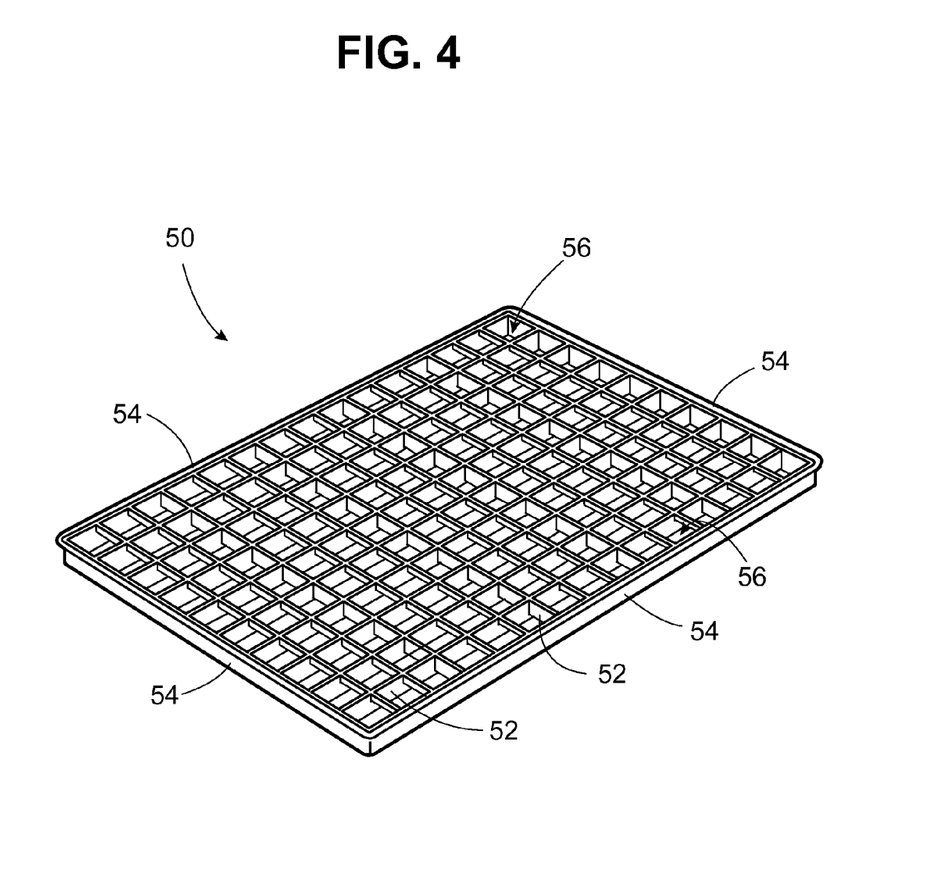
FIG. 4 is a perspective schematic view of an egg flat capable of containing eggs in a fixed position.

Referring to FIG. 4, the egg flat 50 may be formed of a plurality of intersecting slats 52 confined by a plurality of ends 54. The slats 52 may define a plurality of open-ended pockets 56, with each pocket 56 capable of receiving an end of a respective egg 1. In some instances, the narrow end 10 (FIGS. 1 and 2) of the egg 1 may be received within the pocket 56 such that the blunt end 20 projects above the egg flat 50.

Figure 5:
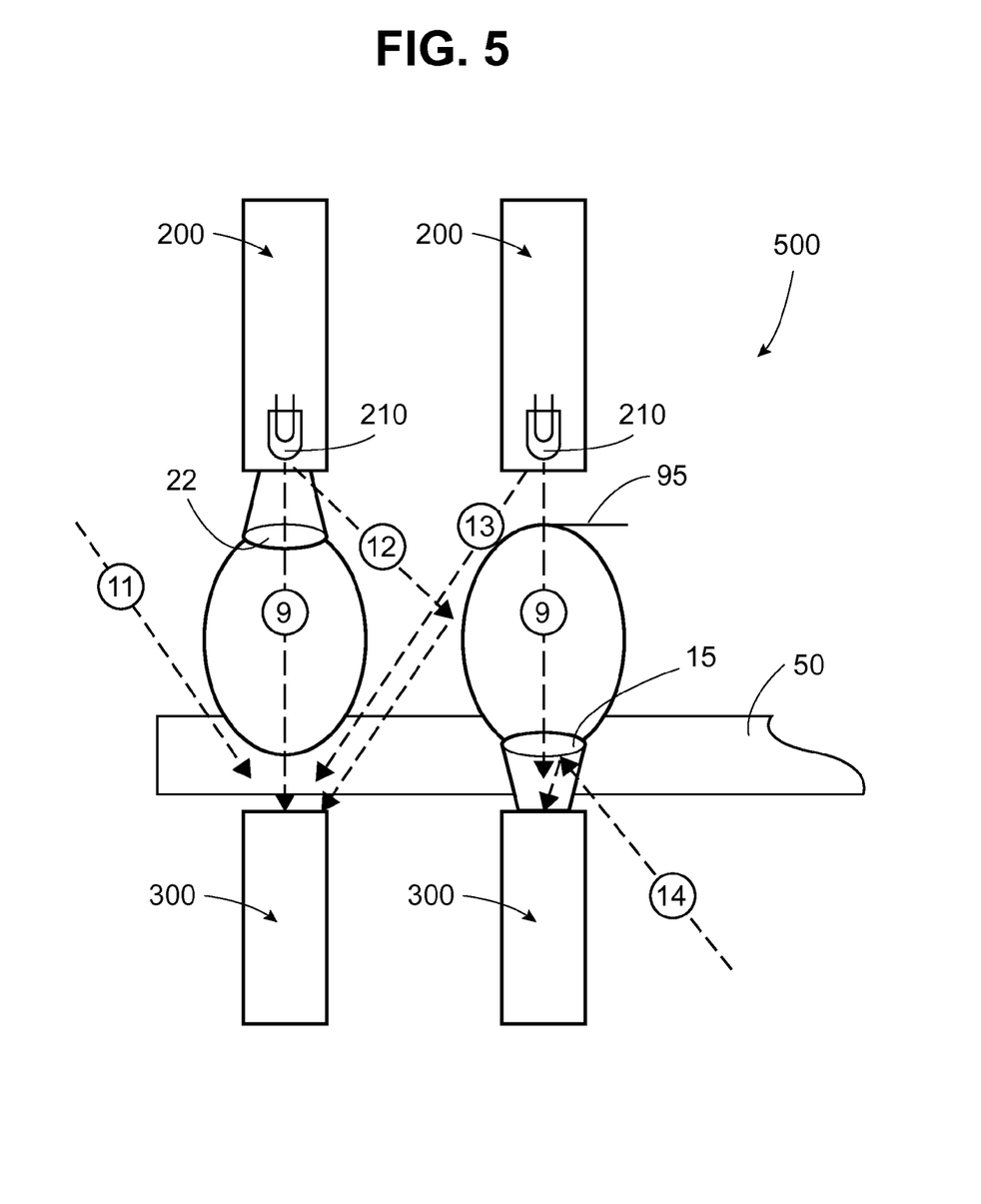
FIG. 5 illustrates eggs in an egg flat being conveyed past a series of emitter-detector pairs of an egg detection system, and further illustrating paths of interference off-axis emissions that undesirably contribute to a detected signal.
Figure 6:
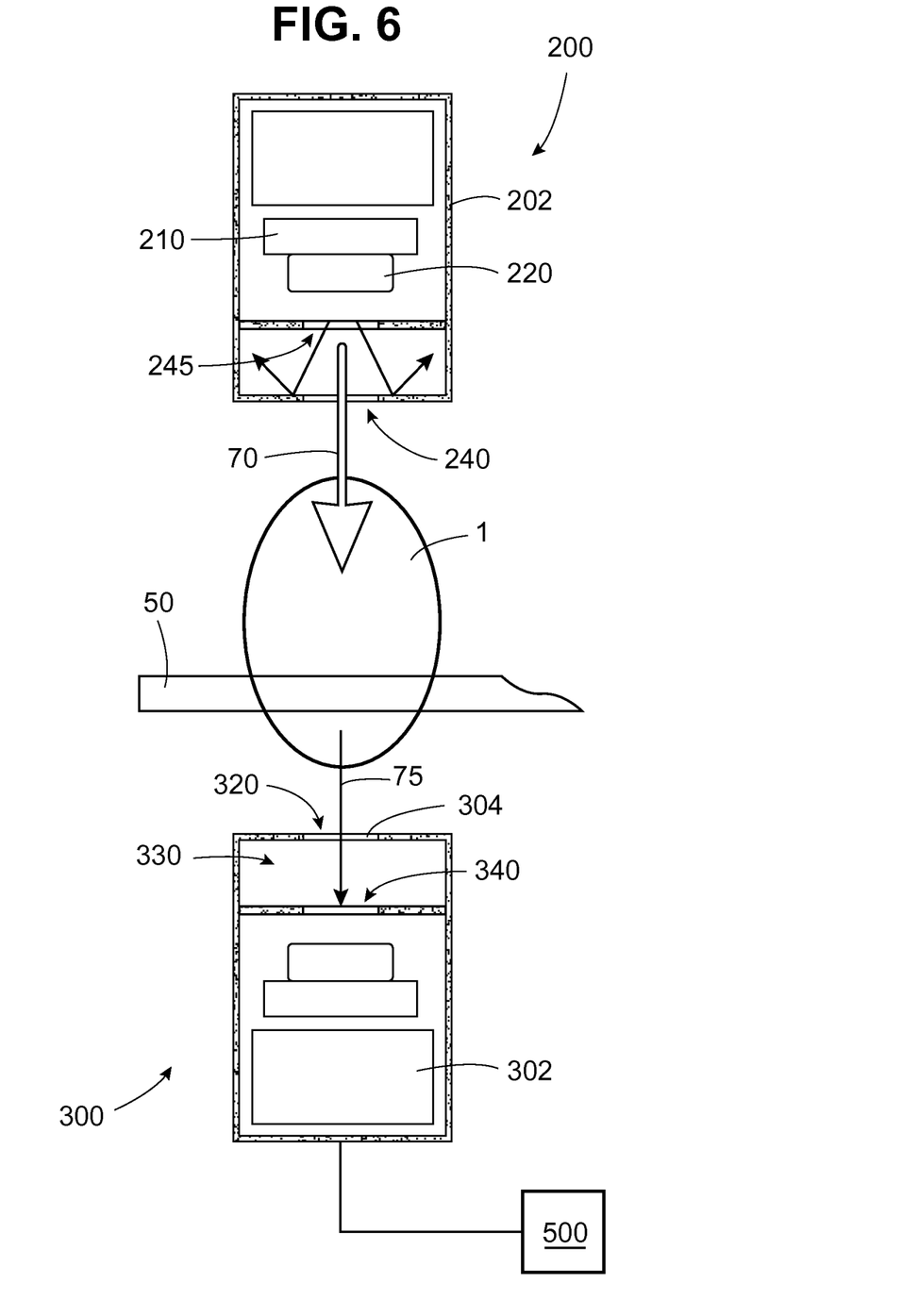
FIG. 6 illustrates an egg being investigated for viability by an emitter-detector pair capable of use in an egg detection system, according to one aspect of the present disclosure.

Referring now to FIGS. 5 and 6, an emitter-detector pair 500 for use in classifying eggs, according to some aspects of the present disclosure, is illustrated. The illustrated emitter-detector pair 500 may include an emitter assembly 200 and a detector assembly 300. In operation, a plurality of the emitter-detector pairs 500 may be arranged in an array and utilized to classify a respective array of eggs supported by an egg flat 50 (FIG. 4). The illustrated emitter assembly 200 may include a cylindrical emitter housing 202. Aspects of the present disclosure are not limited to the illustrated configuration of the emitter housing 202. The emitter housing 202 may have various shapes, sizes and configurations without limitation. An array of the emitter assemblies 200 may be supported via a frame or other supporting member of the egg detection system 160. Because the egg detection system 160 operates in a non-contact manner, the emitter assemblies 200 may not need to move between a raised position and a lowered position, although in some instances each may be configured for such.

Disposed within the emitter housing 202 is a light emission source 210. The light emission source 210 may be configured to emit electromagnetic radiation of various wavelengths of the electromagnetic spectrum, including, for example, visible light, infrared light and near-infrared light. In some instances, the light emission source 210 may be particularly configured to emit infrared light in the wavelength range of about 820-860 nanometers (nm), and more particularly at about 850 nm. According to some aspects, the light emission source may be formed of a light emitting diode (LED) configured to emit light from the infrared portion of the electromagnetic spectrum. However, aspects of the present disclosure are not limited to the use of LEDs or infrared radiation. Various types of light emission sources may be utilized without limitation. As one example, the light emission source may be a surface mount package such as model SFH 4259 LED in a SMT Power TopLED package from OSRAM. Another example of a light emission source may be a laser diode source or a solid-state excitation source.

FIG. 5 illustrates the various potential emission paths that the electromagnetic radiation emitted by the light emission source 210 may travel when exiting the emitter assembly 200. As mentioned previously, detecting the low transmitted light levels 10 transmitted through the egg 1 without the use of a mechanical light seal provides a challenge when evaluating viability of the egg 1 based upon an embryo heartbeat. In light of the absence of mechanical light seals, aspects of the present disclosure may be configured to minimize the generation of interfering reflective signals 12 from the same source as well as those adjacent emitter signals 13 from adjacent emitter assemblies, to maximize the rejection of interfering reflective signals 12 and adjacent emitter signals 13, to maximize the rejection of ambient lighting signals 11, and to minimize signals 14 from impinging on a detector field of view (FOV) 15 of the detector assembly 300. In this regard, aspects of the present disclosure may be configured to maximize desired signal collection while simultaneously maximizing rejection of undesired signals to attain a desired signal-to-interference (S/I) ratio.

The emitter assembly 200 may be configured to maximize emission of the electromagnetic radiation along a longitudinal axis of the egg 1 such that the emissions are directed toward the egg 1, while also maximizing rejection of off-axis emissions. That is, the emitter assembly 200 may be configured to collimate the light into a directed beam, rather than focusing the beam, so as to project the emission of the light emission source 210 onto a prescribed region of the egg 1, while limiting the emission of stray light, wherein stray light is any optical energy leaving the emitter assembly 200 that does not illuminate the prescribed region of the egg (or light that reflects from the prescribed region of the egg).

In some instances, the light emission source 210 may be a narrowband light source in order to differentiate the transmitted light 9 from the ambient light 11. According to some aspects, the light emission source 210 may emit radiation at wavelengths that distinguish the source from the ambient light 11. Further, the light emitted from the light emission source 210 may be modulated at discrete (and, in some instances, unique) frequencies to separate the desired transmitted signal 10 from adjacent emitter signals 13 and ambient light signals 11 in the electrical domain. In addition, the light emitted from the light emission source 210 may be modulated with a sinusoidal power variation in the optical power so as to locate the electrical signal power within a narrow frequency band, which may enable signal recovery with analog and digital filtering techniques.

Figure 7:
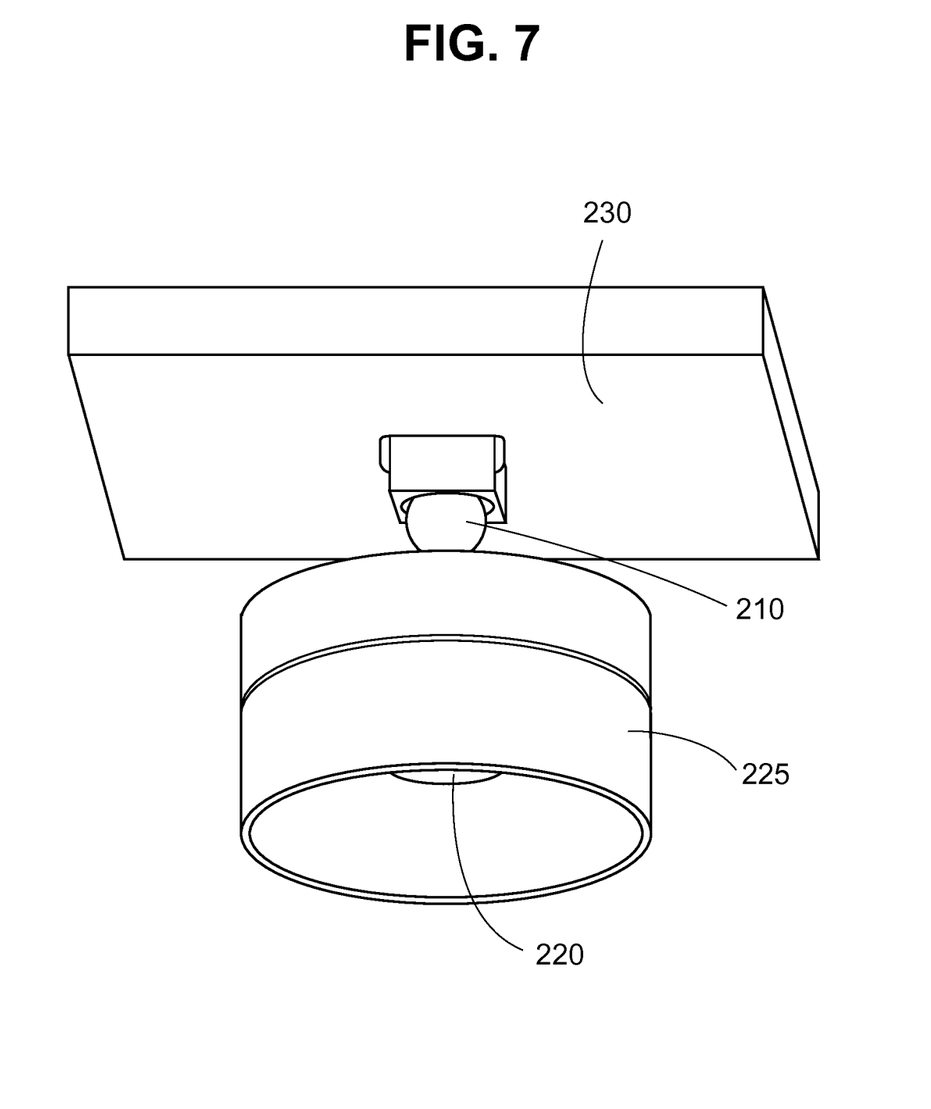
FIG. 7 illustrates a light emitting source and associated collimator device forming a portion of an emitter assembly capable of use in an egg detection system, according to one aspect of the present disclosure.
Figure 8:
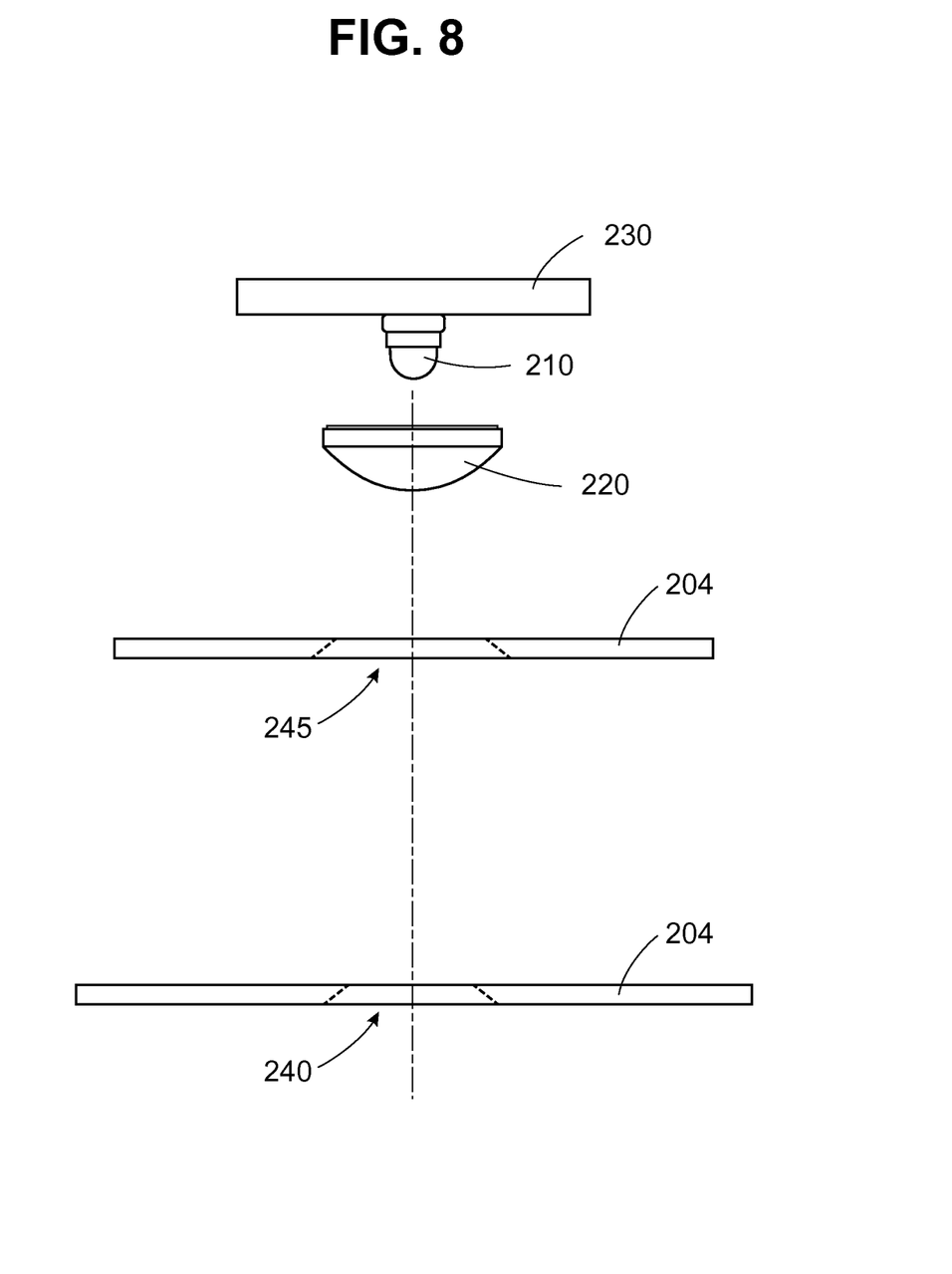
FIG. 8 illustrates various components of an emitter assembly capable of use in an egg detection system, according to one aspect of the present disclosure.

As shown in FIGS. 6-8, the emitter assembly 200 may be configured to collimate, as opposed to focusing, emissions from the light emission source 210 to minimize interfering reflective signals 12 and adjacent emitter signals 13. According to some aspects, an emitter field of view 22 may be selected to be about equal to the detector field of view 15, which in some instances may be a circular region eight (8) millimeters in diameter. A small emitter field of view 22 may leave the system intolerant to localized non-uniformities such as dirt and debris on the surface of the egg 1, while too large of an area may diffuse the optical flux, reducing the signal throughput. In the interest of maximizing the signal throughput and reducing the scatter of light from the egg surface, the emissions from the light emission source 210 may be collimated. Light that is not collimated from the light emission source 210 may be attenuated so as to minimize the contamination of the local environment with stray light.

A collimator device may be provided to collimate the electromagnetic radiation emitted from the light emission source 210. In some instances, the collimator device may be, for example, a lens, a total internal reflectance (TIR) parabolic reflector, a condenser lens or a laser diode. According to some aspects, the collimator device 220 may be aspheric. Multiple collimator devices 220 may be used in some configurations. According to one aspect, an emitter lens 220 may include a lens housing 225 for mounting the emitter lens 220 proximate to the light emission source 210. As shown in FIG. 7, the light emission source 210 may be mounted to a printed circuit board (PCB) 230.

The stray light control of the emitter assembly 200 refers to reducing light emitted by the light emission source 210 that does not illuminate the emitter field of view 22 on the egg 1. Such undesirable illumination may potentially scatter and make its way to the detector assembly 300 or to an adjacent detector assembly 300 in the case of an array of detector assemblies 300. Minimizing the emission of stray light at the emitter assembly 200 may be considered the first step in reducing stray light at the detector assembly 300. In this regard, the light emission source 210 may be enclosed by the emitter housing 202 so as to minimize the stray light. The emitter housing 202 may be black anodized to help attenuate light at each scatter event. The emitter assembly 200 may include a transparent window at an emitter exit aperture 240 that permits light to pass therethrough.

The emitter housing 202 and one or more apertures or vanes may be used to form an emitter baffle arrangement to control the residual light emitted by the light emission source 210 or scattered by the lens housing 225. According to one aspect, as shown in FIG. 8 (the emitter housing 202 and the emitter lens 220 are removed for clarity), the emitter housing 202 or associated structures 204 thereof may define an emitter exit aperture 240 and one or more emitter internal aperture or vane 245. The emitter exit aperture 240 and the emitter internal vane 245 may constrain the signal to the desired collimated beam, while rejecting any signal outside of the beam diameter. Increasing the length of the emitter assembly 200 along with the addition of more emitter internal vanes 245 may improve the stray light rejection. The emitter housing 202 and other components of the emitter assembly 200 may have a finish that reduces the reflection of emitted light. For example, the emitter housing 202 may have a black anodize surface finish. In some instances, with an 8 millimeter emitter field of view 22, the range of axial distance between a plane 95 of the egg 1 at the blunt end 20 and the emitter exit aperture 240 may be between about 10 to 60 millimeters. In some instances, shaping, texturing, or coating the front face of the emitter assembly 200 may be provided to reduce emission of undesirable light into the environment.

The present disclosure may also include a detector assembly 300 for receiving electromagnetic radiation/light transmitted through the egg during the candling operation. The detector assembly 300 may be positioned opposite the emitter assembly 200 in an axial alignment so as to form an emitter-detector pair. Thus, a plurality of emitter assemblies 200 and a respective plurality of detector assemblies 200 may form an array of emitter-detector pairs capable of evaluating a plurality of eggs transported in an egg flat.

As discussed previously, in some instances, the detector assembly 300 may be spaced-apart from the egg during the candling operation such that no part of the detector is in contact with the egg, thereby defining a non-contact position. Such a contactless configuration may allow for increased throughput and may limit contamination of subsequent eggs, as described previously. Thus, to provide a contactless feature, it may be desirable to maximize the collection of light emitted by the egg 1 from within a specified angular detector field of view, which represents the output signal, while minimizing the light collected from outside of the detector field of view. In some instances, the detector assembly 300 may be separated from the egg 1 at between about 10 to 100 millimeters, and more specifically at about 19 millimeters.

The detector assembly 300 may include photodetection means for detecting and carrying out photoelectric conversion of the light transmitted through the egg. For example, a sensor 302 having a photodetector (e.g., a PIN diode) for generating an output signal corresponding to the intensity of the light leaving an egg. The sensor 302 may be any type of sensor capable of detecting the wavelength(s) of light emitted by the light emission source 210 at modulation frequencies, including DC. According to some aspects, detector assembly 300 may not use any optical elements to collect the optical energy from the egg 1, so as to be a so-called "passive" sensor. In general, the purpose of the sensor 302 may be to detect illumination emitted from a restricted region (field of view) of the egg 1. Light entering the sensor 302 with an angle greater than the angular detector field of view and illuminating the sensor 302 may contribute an unwanted response that degrades the system response.

In some instances, the detector field of view 15 may be particularly specified to be an eight millimeter diameter region at the narrow end 10 of the egg 1, wherein the detector field of view may be measured on a plane 90 tangent to narrow end 10 of the egg 1. The detector assembly 300 may have a square active area and an integrated long pass or bandpass wavelength optical filter, such as, for example, an integrated near-infrared pass filter capable of rejecting wavelengths or undesired light.

The detector assembly may include a detector housing 310 and a transparent window 304 that permits light to pass therethrough. The transparent window 304 may be formed from various types of material, without limitation. Exemplary materials include, but are not limited to, glass, sapphire, and plastic (e.g., non-reflecting, transparent plastic, etc.). The sensor 302 may be disposed within the detector housing 310 and receives light leaving an egg through the window 304. The window 304 may be secured to the detector housing 310 in various ways to ensure that the detector housing 310 remains substantially waterproof.

Figure 9:
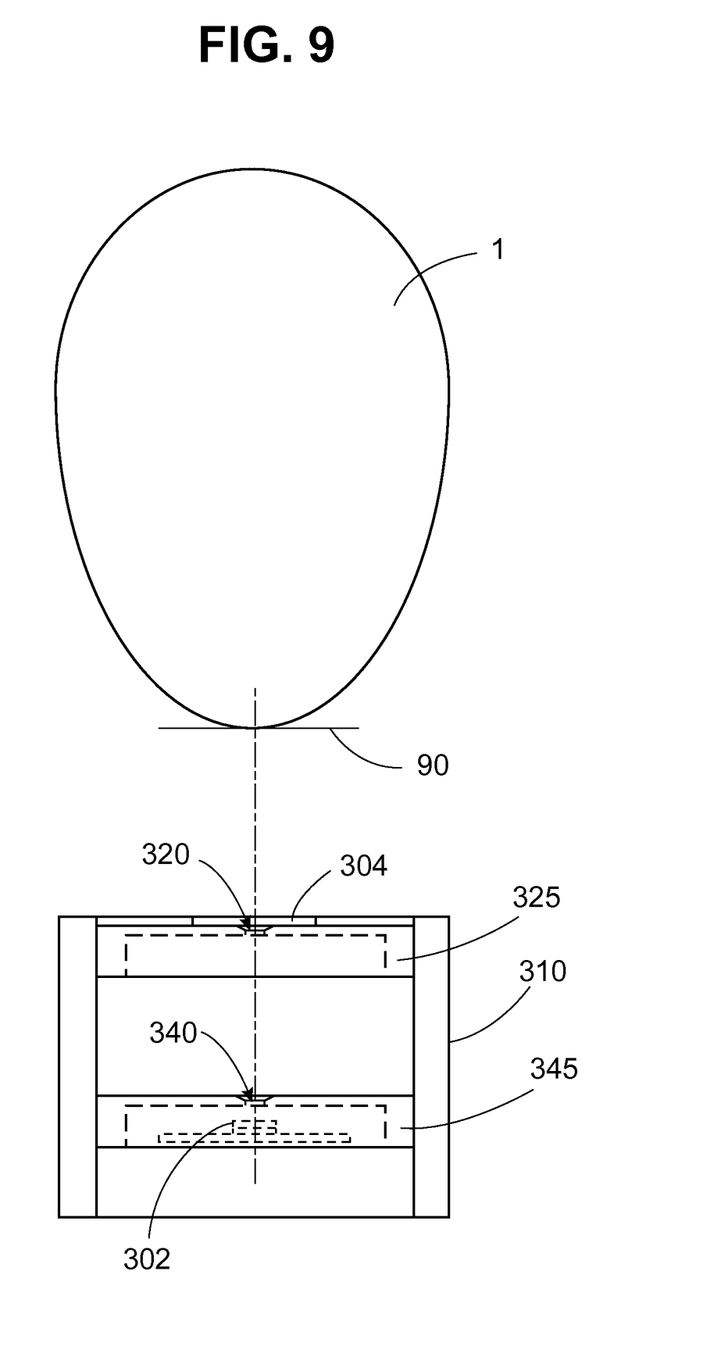
FIG. 9 illustrates a detector assembly in relation to an egg and an associated egg detection plane, according to one aspect of the present disclosure.

The detector assembly 300 may include a detector baffle arrangement 330 within the detector housing 310 and having one or more vanes and apertures for rejecting stray or off-axis light capable of entering the detector assembly 300 along undesired paths, while allowing desired transmitted light to be collected from the detector field of view on the narrow end 10 of the egg 1. According to one aspect, as shown in FIG. 9, the detector assembly 300 may include two apertures 320 and 340, which serve as the field stop 325 and the aperture stop 345 for the sensor 302. The field stop 325 limits the detector field of view, while the aperture stop 345 limits the light to only that that can directly reach the sensor 302 and rejects/ stops light that would otherwise fall immediately adjacent to the sensor 302. In some instances, the aperture edges may have, for example, a 0.25 millimeter radius. It was found that a smaller radius of the edge of the aperture 320 may improve stray light performance since the aperture edge radius feature on the field stop 325 may contribute greatly to the stray light signal. In some instances, in order to reduce the stray light, the edges of the apertures 320 and 340 may be sharpened, particularly with respect to the aperture 320 of the field stop 325.

In some aspects, the aperture 340 may be defined as a circular aperture to ensure a circular detector field of view to control stray light. The diameter of the aperture 340 (the aperture stop 345) may be slightly smaller than the full width of the sensor 302 so as to ensure that all signal passing through the aperture stop 345 may then be incident on the surface of the sensor 302. With this geometry, the dimension of the aperture stop 345 and location define the effective detection region for the sensor 302. With the detector field of view and the sensor size established, the throughput may be optimized by controlling the separation between the field stop 325 and the aperture stop 345. Such separation may be between about 12 to 26 millimeters, or more specifically between about 15 to 20 millimeters, or more particularly at about 17 millimeters. The two aperture diameters may be adjusted to maintain a constant detector field of view and detector size over the separation range. In some instances, the field stop 325 may have a field stop aperture radius of between about 1.0 to 1.5 millimeters, or more particularly at about 1.3 millimeters. In some instances, the aperture stop 345 may have an aperture stop radius of between about 0.5 to 1.0, or more particularly at about 0.8 millimeters.

Figure 10:
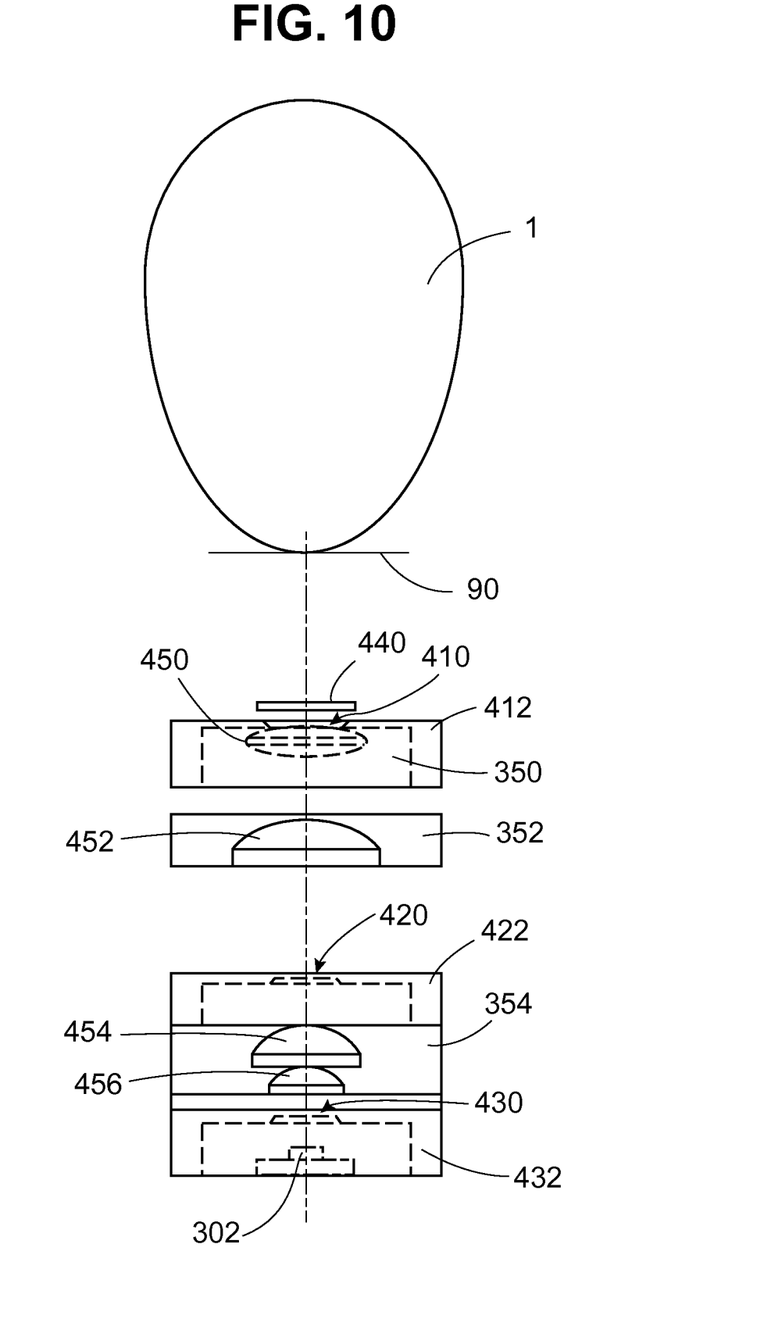
FIG. 10 illustrates a detector assembly in relation to an egg and an associated egg detection plane, according to another aspect of the present disclosure.

According to some aspects, as shown in FIG. 10 (with the detector housing 310 removed for clarity), the detector assembly 300 may utilize optical elements or a detector lens system to collect light from a prescribed region on the egg 1 (the detector field of view) and deliver it to the sensor 302. In this regard, mechanical features such as apertures and lens cells may be included to improve performance of the detector assembly 300. According to one aspect, three apertures may be included in the configuration of the detector assembly 300. These may be referred to as an entrance aperture 410, a field stop aperture 420, and a detector aperture 430 (with corresponding stops 412, 422, 432, respectively). The detector assembly 300 may also utilize one or more lens elements mounted within lens cells to form the detector lens system. The presence of the lens cells may impact the performance of the detector assembly 300 by directing more collected light on the sensor to increase the sensitivity thereof. Unfortunately, the presence of the lens cells may also increase the stray light contribution. However, the increase in the desired signal is greater than the increase in the interfering signal, thereby leading to an improved signal-to-interference ratio. In some instances, the aperture edges may have, for example, a 0.25 millimeter radius. A protective window 440 may be included to protect the components disposed within the detector housing 310.

In some instances, the detector lens system may particularly include four lenses 450, 452, 454, 456 to collect light for delivery to the sensor 302. However, it should be noted that the detector lens system may, in some instances, eliminate lenses 452 and 456 such that the only lenses used are lenses 450 and 454, wherein a single custom lens may replace a lens pair.

As shown in FIG. 10, in this particular aspect, the detector lens system may include a plurality of lens cells 350, 352, 354, wherein the lens 450 may be disposed within lens cell 350, the lens 452 may be disposed within lens cell 352, and lenses 454 and 456 may be disposed within lens cell 354. According to one particular aspect, lenses 450, 452, 454 and 456 may have focal lengths of about 20 millimeters, 25 millimeters, 15 millimeters and 8 millimeters, respectively. In some instances, the lens 450 may be distanced about 0.05 to 0.15 millimeters from the entrance aperture stop 412; the lens 452 may be distanced between about 11.5 and 12.0 millimeters from the entrance aperture stop 412; the lens 454 may be distanced between about 6 to 7 millimeters from the field aperture stop 422; and the lens 456 may be distanced between about 11 to 12 millimeters from the field aperture stop 422. In some instances, the field aperture stop 422 may be distanced between about 30 to 35 millimeters from the entrance aperture stop 412, and more particularly at about 32 millimeters, while the detector apertures stop 432 may be distanced between about 45 to 50 millimeters from the entrance aperture stop, and more particularly at about 49 millimeters; wherein the sensor 302 may be distanced from the entrance aperture stop between about 45 to 55 millimeters, and more particularly at about 50 millimeters.

According to some aspects, the aperture radius of the entrance aperture may be between about 5.0 to 6.0 millimeters, or more particularly at about 5.7 millimeters. In some instances, the aperture radius of the field stop aperture may be between about 3.0 to 4.0 millimeters, or more particularly at about 3.6 millimeters. In some instances, the aperture radius of the detector aperture may be between about 1.0 to 2.0 millimeters, or more particularly at about 1.5 millimeters.

According to some embodiments, the detector assembly 300 may implement a long-pass or band pass optical filter in front of the sensor 302 to minimize the effect of ambient light. Such a filter may be discrete or configured into the detector assembly 300. According to some aspects, the detector assembly 300 may use a narrow bandpass electrical signal to reject undesired signals. In some instances, the sensitivity of the detector assembly 300 may be determined by the bandwidth of such a filter. According to some embodiments, the detector assembly 300 may include a low noise amplifier to increase the signal levels that may be sampled. According to some aspects, an envelope detector may be used to recover information from a modulated signal, wherein a down converter/mixer may optionally be used for such recovery. According to some aspects, an analog-to-digital converter may be used to sample the detected signal for subsequent digital processing.

In operation, once an egg 1 is disposed between the emitter-detector pair, the light emission source 210 may emit light (indicated as 70 in FIG. 6) into the egg 1. The sensor 302 may receive light that leaves the egg 5 (indicated as 75 in FIG. 6) and may generate an output signal corresponding to the intensity of the light leaving the egg 1.

A processor 500 may be in communication with the detector assembly 300 and configured to process output signals from the sensor 302 to determine the viability of the egg 1. Eggs having an embryo pulse may be designated as live eggs. Viability may be determined by processing the output signal to determine the existence of variations in light intensity that correspond to an embryo pulse or embryo movement.

For example, in some instances, viability may be determined by processing the output signal to determine the existence of cyclical or periodic variations in light intensity that correspond to an embryo pulse. This type of signal may typically be produced by movement of the embryo heart and blood displacement within the vascular areas of the embryo. Periodic signals may lend themselves to electrical filtering and signal processing techniques that allow them to be separated from aperiodic signals, including background mechanical movement (e.g. motor vibration, operator handling, etc.). As used herein, periodic variation refers to a signal that may have some variation and may not be truly periodic. That is, the frequency between heartbeats of the embryo may vary due to many factors, but is still considered a cyclical signal that can be easily interpreted as a heartbeat signal. The detection of the periodic signal may occur in the frequency domain.

In other instances, viability may be determined by processing the output signal to determine the existence of aperiodic variations or perturbance in light intensity that corresponds to embryo movement. This type of signal may be produced by a single heartbeat but can be produced when the embryo shifts position within the egg. This type of signal may be difficult to distinguish from signals created by background mechanical movement. The motion of the embryo within the egg may change the amount of light that is transmitted through the egg. The detected signal may then show a change in amplitude. The detection of the aperiodic signal may occur in the time domain.

The signal from a non-live egg may be generally identified as constant and may not include any variations in the signal, other than potential interfering signals or noise. That is, for a non-live egg, there will not be any corresponding heartbeat or embryo movement to detect.

According to some aspects, the processor 500 may use signal processing techniques such as, for example, Fast Fourier Transform (FFT) or Discrete Fourier Transform (DFT) to identify periodic (heartbeat) patterns within the detected signal. According to some aspects, the processor 500 may use over-sampling and windowing to average random noise in the frequency transformation to more accurately identify the periodic (heartbeat) signal.

According to some aspects of the present disclosure, the egg detection system 160 may be capable of identifying eggs according to viability while being moved through the egg identification system 100. In this regard, the eggs 1 in the egg flat 50 may be capable of being moved through the egg identification system 100 during viability evaluation thereof, thereby allowing for an optimal throughput as desired. To that end, the egg flat 50 may need to be stopped or paused during identification processing to allow for sufficient data collection. In some instances, the detection time for detecting an aperiodic signal may be less than the detection time for detecting a periodic signal.

While the blunt end 20 of the egg 1 is shown and described as being irradiated, it is possible that the positions of the emitter assembly 200 and the detector assembly 300 may be switched such that the electromagnetic radiation is directed upward into the narrow end 10 of the egg 1 and the transmitted light detected at the blunt end 20. Furthermore, in some instances, the eggs may be in an angular orientation with respect to the common axis of the axially aligned emitter-detector pair. Particularly, in some instances, the egg may be positioned relative to the emitter-detector pair such that a longitudinal axis of the egg is perpendicular to the common axis of the emitter-detector pair. In this manner, the egg may be presented "sideways" to the emitter-detector pair for identification.

Figure 11:
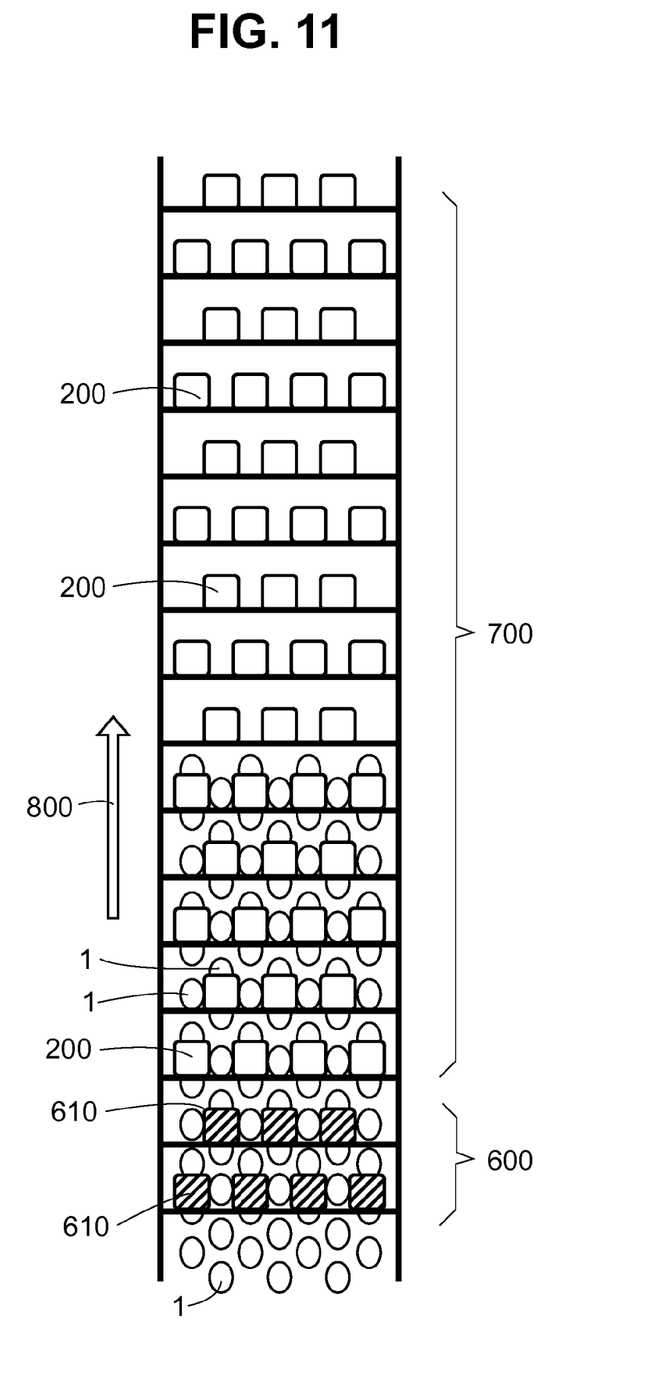
FIG. 11 illustrates a plurality of eggs being conveyed through an egg detection system having an opacity detection component and a heartbeat detection component, according to one aspect of the present disclosure.

According to some aspects, as shown in FIG. 11, the egg detection system 160 may include an opacity identification system 600 and a heartbeat detection system 700. The heartbeat detection system 700 is represented by the aspects previously described with respect to FIGS. 5-10. In some instances, the opacity identification system 600 may be provided upstream in a processing direction 800 from the heartbeat detection system 700. The opacity identification system 600 may include an emitter assembly (individual emitters 610) located above the conveyed egg flats 50 and a receiver assembly located below the conveyed egg flats 50. The opacity identification system 600 scans eggs and identifies the eggs as non-viable (clear) or viable (non-clear) before being conveyed to the heartbeat detection system 700. Each emitter 610 may direct light down though each egg 1 and a receiver gathers the light passed through the egg. Light passing through each egg 1 may be measured to determine if the egg is non-viable or viable.

In this regard, the opacity identification system 600 may be used as a first-pass identifier to identify clear eggs, early-dead eggs, or eggs missing from the egg flat 50 before passing them through the heartbeat detection system 700. In order to limit saturation of the detector assemblies 300 of the heartbeat detection system 700, respective positions of the emitter-detector pairs may be turned-off, deactivated, or otherwise disabled when associated with eggs 1 identified by the opacity identification system 600 as, for example, clear, early-dead, or missing. That is, eggs 1 that are clear, early-dead, or missing may undesirably allow significant amounts of transmitted light to reach the detector assembly 300. As such, the opacity identification system 600 may be in communication with the controller of the egg identification system 100 such that the controller may selectively direct operation of the emitter assembly 200 and/or the detector assembly 300 associated with the heartbeat detector system 700. In this manner, detector saturation may be minimized by communicating to the controller that certain emitter-detector pairs should be disabled for a given egg flat 50.

According to some aspects, each egg may undergo evaluation and identification by more than one emitter-detector pair when passing through the heartbeat detection system 700 to further ensure improved accuracy of the identification system.

The systems and methods described herein may also be referred to as non-invasive in that egg shell structure remains intact throughout the evaluation of the egg. Furthermore, aspects of the present disclosure do not require substances to be introduced into the egg shell or the internal components of the egg in order to evaluate the egg for viability, although in some instances such substances, such as biomarkers, may be introduced prior to evaluation. Such aspects involving the introduction of one or more substances, however, would be considered invasive.

Many modifications and other aspects of the present disclosure set forth herein will come to mind to one skilled in the art to which this disclosure pertains having the benefit of the teachings presented in the foregoing descriptions and the associated drawings. Therefore, it is to be understood that the present disclosure is not to be limited to the specific aspects disclosed and that modifications and other aspects are intended to be included within the scope of the appended claims. Although specific terms are employed herein, they are used in a generic and descriptive sense only and not for purposes of limitation.

That which is claimed:

1. An egg identification system for determining viability of an avian egg, comprising:
    a conveyor system configured to convey an egg flat containing a plurality of eggs;
    an emitter assembly configured to emit collimated electromagnetic radiation toward one of the eggs conveyed in the egg flat;
    a non-contact detector assembly axially aligned with the emitter assembly, the non-contact detector assembly being configured to detect the electromagnetic radiation transmitted through the egg, the non-contact detector assembly being disposed in a non-contact position such that an egg positioned for identification is spaced-apart from the non-contact detector assembly during operation thereof;
    a processor configured to process an output signal of the non-contact detector assembly to determine whether there exists at least one of a periodic and aperiodic variation in an intensity of the electromagnetic radiation transmitted through a respective egg corresponding to action of a heart or embryo movement, the existence of one of the periodic and aperiodic variations indicating that the egg is viable; and
    an opacity identification assembly configured to determine viability of the eggs based upon an opacity associated with a respective egg, the opacity identification assembly being disposed upstream of the emitter assembly and the non-contact detector assembly, the opacity identification assembly being in communication with a controller configured to disable operation of the emitter assembly and the non-contact detector assembly when a non-viable egg, as identified by the opacity identification assembly, is disposed therebetween for viability determination.

2. An egg identification system according to claim 1, wherein the emitter assembly comprises a collimator device configured to collimate the electromagnetic radiation emitted therefrom.

3. An egg identification system according to claim 1, wherein the emitter assembly comprises an emitter housing having an emitter baffle arrangement configured to reject off-axis electromagnetic radiation emitted from the emitter assembly.

4. An egg identification system according to claim 1, wherein the emitter assembly comprises a modulator configured to modulate the electromagnetic radiation emitted therefrom in the form of a modulated signal.

5. An egg identification system according to claim 1, wherein the emitter assembly includes a light emitting diode source configured to emit infrared radiation.

6. An egg identification system according to claim 1, wherein the non-contact detector assembly comprises a detector housing having a detector baffle arrangement configured to reject undesired electromagnetic radiation from being received by the non-contact detector assembly for generating the output signal.

7. An egg identification system according to claim 1, wherein the non-contact detector assembly comprises a detector lens system configured to collect the electromagnetic radiation transmitted through the egg.

8. A method of determining viability of an egg, the method comprising:
    conveying an egg contained in an egg flat using a conveyor system;
    emitting collimated electromagnetic radiation from an emitter assembly toward the egg;
    detecting electromagnetic radiation transmitted through the egg with a non-contact detector assembly axially aligned with the emitter assembly, the non-contact detector assembly being spaced-apart from the egg;
    generating an output signal from the electromagnetic radiation detected by the non-contact detector assembly;
    processing the output signal to determine whether there exists at least one of a periodic and aperiodic variation in an intensity of the electromagnetic radiation transmitted through a respective egg corresponding to action of a heart or embryo movement, the existence of one of the periodic and aperiodic variations being indicative that the egg is viable;
    conveying the egg through an opacity identification assembly configured to determine viability of the eggs based upon an opacity associated with the egg, the opacity identification assembly being disposed upstream of the emitter assembly and the non-contact detector assembly; and
    disabling operation of the emitter assembly and the non-contact detector assembly when a non-viable egg, as identified by the opacity identification assembly, is conveyed thereto for viability determination.

9. A method according to claim 8, wherein emitting electromagnetic radiation from an emitter assembly toward the egg comprises collimating the electromagnetic radiation with a collimator device.

10. A method according to claim 8, further comprising rejecting off-axis electromagnetic radiation emitted from the emitter assembly by using an emitter baffle arrangement disposed within an emitter housing of the emitter assembly.

11. A method according to claim 8, wherein emitting electromagnetic radiation from an emitter assembly comprises modulating the electromagnetic radiation emitted from the emitter assembly in the form of a modulated signal.

12. A method according to claim 8, wherein emitting electromagnetic radiation from an emitter assembly comprises emitting infrared radiation with a light emitting diode source.

13. A method according to claim 8, wherein detecting electromagnetic radiation transmitted through the egg with a non-contact detector assembly comprises rejecting undesired electromagnetic radiation from being received by the non-contact detector assembly by using a detector baffle arrangement disposed within a detector housing of the non-contact detector assembly.

14. A method according to claim 8, wherein detecting electromagnetic radiation transmitted through the egg with a non-contact detector assembly comprises collecting the electromagnetic radiation transmitted through the egg with a detector lens.

* * * * *